(12) United States Patent
Bischof et al.

(10) Patent No.: US 11,976,036 B2
(45) Date of Patent: May 7, 2024

(54) SYNTHESIS OF N-HEPTANE FROM OLEFINS AND RELATED PRODUCTION SYSTEMS

(71) Applicant: Chevron Phillips Chemical Company LP, The Woodlands, TX (US)

(72) Inventors: Steven M. Bischof, Humble, TX (US); Jeffery C Gee, Kingwood, TX (US); James Hillier, Kingwood, TX (US); Kamaljeet Kaur, Katy, TX (US); Ronald C. Smith, Conroe, TX (US); Darin B. Tiedtke, Kingwood, TX (US); Mark L. Hlavinka, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

(21) Appl. No.: 18/338,401

(22) Filed: Jun. 21, 2023

(65) Prior Publication Data
US 2024/0034702 A1    Feb. 1, 2024

Related U.S. Application Data

(62) Division of application No. 17/874,354, filed on Jul. 27, 2022, now Pat. No. 11,731,921.

(51) Int. Cl.
| | | |
|---|---|---|
| *B01J 19/24* | (2006.01) | |
| *B01D 3/14* | (2006.01) | |
| *B01J 21/08* | (2006.01) | |
| *B01J 23/30* | (2006.01) | |
| *C07C 5/03* | (2006.01) | |
| *C07C 6/04* | (2006.01) | |

(52) U.S. Cl.
CPC ............... *C07C 6/04* (2013.01); *B01D 3/143* (2013.01); *B01J 19/245* (2013.01); *B01J 21/08* (2013.01); *B01J 23/30* (2013.01); *C07C 5/03* (2013.01); *B01J 2219/0004* (2013.01); *C07C 2521/08* (2013.01); *C07C 2523/30* (2013.01)

(58) Field of Classification Search
CPC ......... C07C 6/04; C07C 5/03; C07C 2521/08; C07C 2523/30; B01D 3/143; B01J 19/245; B01J 21/08; B01J 23/30; B01J 2219/0004
See application file for complete search history.

(56) References Cited

U.S. PATENT DOCUMENTS

| | | |
|---|---|---|
| 4,547,617 A | 10/1985 | Welch |
| 8,680,306 B2 | 3/2014 | Chahen |

(Continued)

FOREIGN PATENT DOCUMENTS

| | | |
|---|---|---|
| GB | 1216278 A | 12/1970 |
| WO | 2022060491 A1 | 3/2022 |

OTHER PUBLICATIONS

Chetty, American Chemical Society Omega 2018, 3, 7911-7924.

(Continued)

*Primary Examiner* — In Suk C Bullock
*Assistant Examiner* — Jason Y Chong
(74) *Attorney, Agent, or Firm* — Merchant & Gould P.C.

(57) ABSTRACT

Processes for producing n-heptane from a mixture of 1-hexene and 1-octene in the presence of a suitable isomerization-metathesis catalyst followed by a hydrogenation step are disclosed. Integrated manufacturing systems for producing n-heptane with minimal waste also are disclosed.

18 Claims, 1 Drawing Sheet

(56) References Cited

U.S. PATENT DOCUMENTS

| | | |
|---|---|---|
| 8,680,307 B2 | 3/2014 | Chahen |
| 8,809,563 B2 | 8/2014 | Holtcamp |
| 10,975,003 B2 | 4/2021 | Jeon |
| 2002/0147374 A1 | 10/2002 | Abazajian |
| 2003/0028063 A1 | 2/2003 | Gartside |
| 2006/0116542 A1 | 6/2006 | Brown |
| 2011/0263917 A1* | 10/2011 | Van Hal .................... C07C 2/76 585/322 |
| 2012/0296129 A1 | 11/2012 | Bogdan |
| 2015/0141722 A1* | 5/2015 | Ramachandran ......... C07C 6/04 585/315 |

OTHER PUBLICATIONS

International Search Report and Written Opinion issued in corresponding PCT Application No. PCT/US2023/070901, dated Oct. 20, 2023, 10 pp.

* cited by examiner

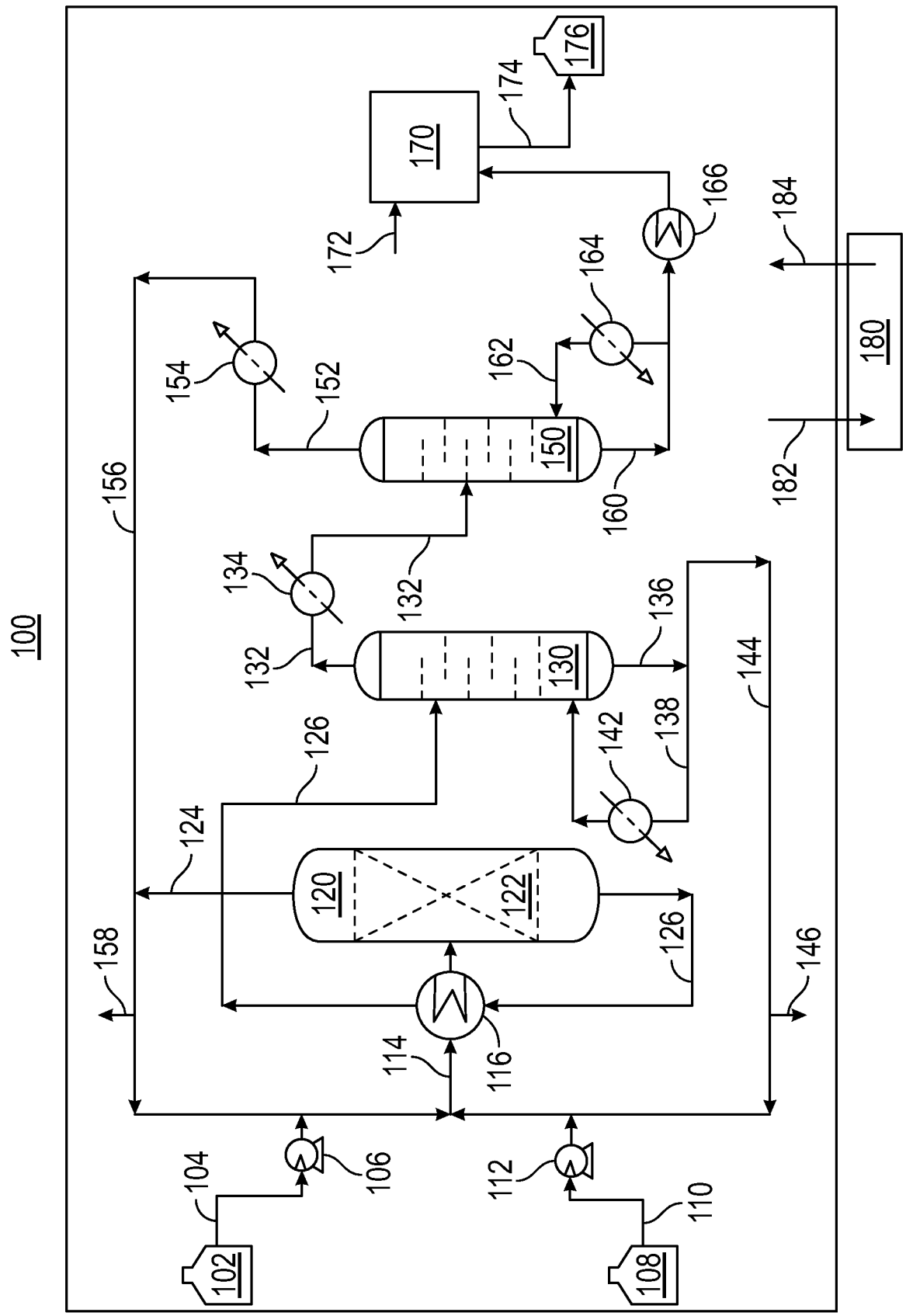

SYNTHESIS OF N-HEPTANE FROM OLEFINS AND RELATED PRODUCTION SYSTEMS

REFERENCE TO RELATED APPLICATION

This application is a divisional application of U.S. patent application Ser. No. 17/874,354, filed on Jul. 27, 2022, now U.S. Pat. No. 11,731,921, the disclosure of which is incorporated herein by reference in its entirety.

FIELD OF THE INVENTION

The present disclosure relates to methods and manufacturing systems for producing n-heptane from an olefin feed stream, and more particularly, relates to such methods and systems in which the olefin feed stream contains 1-hexene and 1-octene.

BACKGROUND OF THE INVENTION

Currently, n-heptane in high purity can be prepared from a refinery feed that is heavily distilled and subsequently hydrogenated. However, this and other current synthesis options typically result in significant by-products, low yields, and poor cost effectiveness. New methodologies for producing n-heptane without these drawbacks are therefore desirable. Accordingly, it is to these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes and manufacturing systems for producing n-heptane are described herein. A representative process to produce n-heptane can comprise (a) subjecting a feed mixture comprising 1-hexene and 1-octene to isomerization-metathesis to form a reaction mixture containing $C_7$ olefins, (b) separating the reaction mixture into a $C_7$ olefin stream and a recycle stream, and (c) hydrogenating the $C_7$ olefin stream to form a product stream containing n-heptane.

A n-heptane manufacturing system consistent with the present invention can comprise (i) a reactor configured to produce a reaction mixture containing $C_7$ olefins from a reactor feed stream comprising 1-hexene, 1-octene, and a recycle stream, (ii) a separations system configured to fractionate the reaction mixture into a $C_7$ olefin stream and the recycle stream, and (iii) a hydrogenation unit configured to produce a product stream containing n-heptane from the $C_7$ olefin stream and hydrogen.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

BRIEF DESCRIPTION OF THE FIGURE

The following FIGURE forms part of the present specification and is included to further demonstrate certain aspects of the present invention. The invention may be better understood by reference to this FIGURE in combination with the detailed description and examples.

FIG. 1 illustrates a n-heptane manufacturing system consistent with an aspect of the present invention.

While the inventions disclosed herein are susceptible to various modifications and alternative forms, only a few specific aspects have been shown by way of example in the drawing and described in detail below. The FIGURE and detailed descriptions of these specific aspects are not intended to limit the breadth or scope of the inventive concepts or the appended claims in any manner. Rather, the FIGURE and detailed descriptions are provided to illustrate the inventive concepts to a person of ordinary skill in the art and to enable such person to make and use the inventive concepts.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the systems, compositions, processes, or methods described herein are contemplated with or without explicit description of the particular combination. Additionally, unless explicitly recited otherwise, any aspect or feature disclosed herein can be combined to describe inventive systems, compositions, processes, or methods consistent with the present disclosure.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For instance, a general reference to pentane includes n-pentane, 2-methyl-butane, and 2,2-dimethylpropane; and a general reference to a butyl group includes a n-butyl group, a sec-butyl group, an iso-butyl group, and a t-butyl group.

Unless otherwise specified, the term "substituted" when used to describe a group, for example, when referring to a substituted analog of a particular group, is intended to describe any non-hydrogen moiety that formally replaces a hydrogen in that group, and is intended to be non-limiting. Also, unless otherwise specified, a group or groups can also be referred to herein as "unsubstituted" or by equivalent terms such as "non-substituted," which refers to the original group in which a non-hydrogen moiety does not replace a hydrogen within that group. Moreover, unless otherwise specified, "substituted" is intended to be non-limiting and include inorganic substituents or organic substituents as understood by one of ordinary skill in the art.

The terms "contacting," "subjecting," and the like are used herein to describe systems and methods in which the materials are combined together in any order, in any manner, and for any length of time, unless otherwise specified. For example, the materials can be blended, mixed, slurried, dissolved, reacted, treated, impregnated, compounded, or otherwise combined in some other manner or by any suitable method or technique.

The term "hydrocarbon" refers to a compound containing only carbon and hydrogen, whether saturated or unsaturated. Other identifiers can be utilized to indicate the presence of particular groups in the hydrocarbon (e.g., halogenated hydrocarbon indicates the presence of one or more halogen atoms replacing an equivalent number of hydrogen atoms in the hydrocarbon). Likewise, the term "alkane" refers to a saturated hydrocarbon compound.

The term "olefin" refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" refers to any olefin that has 1) a carbon-carbon double bond between the first and second carbon atom of the longest contiguous chain of carbon atoms, and 2) at least one hydrogen atom bound to the second carbon of the chain. The term "alpha olefin" includes linear and branched alpha olefins and alpha olefins which can have more than one non-aromatic carbon-carbon double bond, unless expressly stated otherwise. The term "normal alpha olefin" refers to a linear aliphatic hydrocarbon mono-olefin having 1) a carbon-carbon double bond between the first and second carbon atoms, and 2) at least one hydrogen atom bound to the second carbon of the chain. The term "linear internal olefin" refers to a linear aliphatic hydrocarbon mono-olefin having a double bond that is not between the first and second carbon atoms.

In this disclosure, while systems and methods are described in terms of "comprising" various components or steps, the systems and methods also can "consist essentially of" or "consist of" the various components or steps, unless stated otherwise. The terms "a," "an," and "the" are intended to include plural alternatives, e.g., at least one.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, the feed mixture or reactor feed stream can contain 1-hexene and 1-octene at different weight ratio ranges in aspects of this invention. By a disclosure that the weight ratio is in a range from 30:70 to 70:30, the intent is to recite that the weight ratio can be any amount in the range and, for example, can include any range or combinations of ranges from 30:70 to 70:30, such as from 35:65 to 65:35, from 35:65 to 50:50, from 40:60 to 60:40, or from 40:60 to 45:55, and so forth. Likewise, all other ranges disclosed herein should be interpreted in a manner similar to this example.

In general, an amount, size, formulation, parameter, range, or other quantity or characteristic is "about" or "approximately" whether or not expressly stated to be such. Whether or not modified by the term "about" or "approximately," the claims include equivalents to the quantities or characteristics.

Although any methods, systems, steps, and components similar or equivalent to those described herein can be used in the practice or testing of the invention, the typical methods, systems, steps, and components are herein described.

All publications and patents mentioned herein are incorporated herein by reference in their entirety for the purpose of describing and disclosing, for example, the constructs and methodologies that are described in the publications and patents, which might be used in connection with the presently described invention.

DETAILED DESCRIPTION OF THE INVENTION

Disclosed herein are processes and systems for producing n-heptane from an olefin feed stream containing 1-hexene and 1-octene. A mixed feed of 1-hexene and 1-octene is introduced into an isomerization-metathesis reactor to form $C_7$ olefins, which are isolated and hydrogenated to produce n-heptane. Both higher and lower carbon number reaction products are recycled, combined with fresh 1-hexene and 1-octene, and fed to the reactor in a closed-loop system, resulting in minimal waste.

Processes for Producing n-Heptane

Aspects of this invention are directed to a process for producing n-heptane. This process can comprise (or consist essentially of, or consist of) (a) subjecting a feed mixture comprising 1-hexene and 1-octene to isomerization-metathesis to form a reaction mixture containing $C_7$ olefins, (b) separating the reaction mixture into a $C_7$ olefin stream and a recycle stream, and (c) hydrogenating the $C_7$ olefin stream to form a product stream containing n-heptane. Generally, the features of this process for producing n-heptane (e.g., the feed mixture, the isomerization-metathesis step and the conditions under which the reaction mixture is formed, the separating step and the conditions under which the separations are performed, and the hydrogenating step and the conditions under which hydrogenation is performed, among others) are independently described herein and these features can be combined in any combination to further describe the disclosed process for producing n-heptane. Moreover, additional process steps can be performed before, during, and/or after any of the steps of this process, and can be utilized without limitation and in any combination to further describe the n-heptane synthesis process, unless stated otherwise.

In step (a), a feed mixture comprising 1-hexene and 1-octene is subjected to isomerization-metathesis to form a reaction mixture containing $C_7$ olefins. Step (a) can be conducted at any suitable temperature and at any suitable pressure. Representative and non-limiting ranges for the temperature of step (a) (or for the formation of the reaction mixture containing $C_7$ olefins) can include from 200° C. to 500° C., from 225° C. to 475° C., from 250° C. to 400° C., from 250° C. to 350° C., from 270° C. to 400° C., or from 270° C. to 350° C. These temperature ranges also are meant to encompass circumstances where step (a) (or the formation of the reaction mixture containing $C_7$ olefins) is performed at a series of different temperatures, instead of at a single fixed temperature, falling within the respective temperature ranges, wherein at least one temperature is within the recited ranges.

While not being limited thereto, isomerization-metathesis step (a) and/or the formation of the reaction mixture containing $C_7$ olefins can be conducted at a reaction pressure in a range from 500 to 2000 psig. Other representative and non-limiting ranges for the reaction pressure can include from 600 to 2000 psig, from 700 to 1800 psig, from 800 to 1600 psig, from 900 to 1500 psig, or from 1000 to 1500 psig, and the like.

Step (a) of the process to produce n-heptane is directed to the isomerization-metathesis of a feed mixture comprising 1-hexene and 1-octene to form a reaction mixture containing $C_7$ olefins. Typically, step (a) is accomplished by contacting the feed mixture with an isomerization-metathesis catalyst to form the reaction mixture, which contains $C_7$ olefins. The isomerization-metathesis catalyst used in step (a) of the process to produce n-heptane is not particularly limited, so long as such catalyst is able to promote the isomerization/metathesis of olefins such as 1-hexene and 1-octene to produce $C_7$ olefins, as described herein. In one aspect, the isomerization-metathesis catalyst can comprise any suitable supported transition metal catalyst. Generally, the transition metal can be supported on any suitable solid oxide or like material. Illustrative examples of solid oxide supports can include silica, alumina, silica-alumina, aluminum phosphate, zinc aluminate, zirconia, thoria, and the like. Combinations of more than one support material can be used for the catalyst.

In one aspect, the isomerization-metathesis catalyst contains tungsten, molybdenum, rhenium, or ruthenium, and the like, as well as any combination thereof. In another aspect, the isomerization-metathesis catalyst contains tungsten; alternatively, molybdenum; alternatively, rhenium; or alternatively, ruthenium. In yet another aspect, the isomerization-metathesis catalyst comprises, consists essentially of, or consists of, a tungsten/silica catalyst. Specific non-limiting examples of suitable isomerization-metathesis catalysts that can be utilized in step (a) are disclosed, for instance, in U.S. Patent Publication Nos. 2003/0028063 and 2006/0116542 and U.S. Pat. Nos. 8,680,306, 8,680,307, and 8,809,563.

Isomerization-metathesis step (a) and/or the formation of the reaction mixture containing $C_7$ olefins often can be a flow process and/or a continuous process. In such circumstances, the feed mixture-catalyst contact time (or reaction time) can be expressed in terms of weight hourly space velocity (WHSV)—the ratio of the weight of the feed mixture which comes in contact with a given weight of catalyst per unit time (units of g/g/hr or $hr^{-1}$). While not limited thereto, the WHSV employed for step (a) can have a minimum value of 0.01, 0.05, 0.1, 0.5, or 1; or alternatively, a maximum value of 5, 4, 3, 2.5, or 2. Generally, the WHSV can be in a range from any minimum WHSV disclosed herein to any maximum WHSV disclosed herein. In a non-limiting aspect, the WHSV can be in a range from 0.01 to 5; alternatively, from 0.05 to 4; alternatively, from 0.1 to 5; alternatively, from 0.1 to 3; alternatively, from 0.1 to 1; alternatively, from 0.5 to 4; alternatively, from 0.5 to 2.5; alternatively, from 0.5 to 2; alternatively, from 1 to 5; or alternatively, from 1 to 3. Other WHSV ranges are readily apparent from this disclosure.

Any suitable reactor or vessel can be used to form the reaction mixture containing $C_7$ olefins in step (a). In a particular aspect, a fixed bed reactor can be used. Accordingly, in this aspect, step (a) can comprise contacting the feed mixture with a fixed bed of an isomerization-metathesis catalyst to form the reaction mixture.

Referring now to the feed mixture in step (a), the weight ratio of 1-hexene:1-octene in the feed mixture generally falls within a range from 30:70 to 70:30. Certain weight ratios of 1-hexene:1-octene in the feed mixture can prove advantageous for improving $C_7$ yield and reducing higher/lower carbon number olefins in the reaction mixture. In one aspect, the weight ratio can range from 35:65 to 65:35, and in another aspect, the weight ratio can range from 35:65 to 50:50, and in yet another aspect, the weight ratio can range from 40:60 to 60:40, and in still another aspect, the weight ratio can range from 40:60 to 45:55.

The $C_7$ olefins in the reaction mixture in step (a) are typically a mixture of $C_7$ internal olefins and $C_7$ alpha olefins, inclusive of 1-heptene (a normal alpha olefin).

The reaction mixture in step (a) contains desirable $C_7$ olefins as well as $C_6-$ olefins (and other hydrocarbons) and $C_8+$ olefins (and other hydrocarbons). In step (b), the reaction mixture is separated into a $C_7$ olefin stream and a recycle stream. This separating step can employ any suitable technique for separating the reaction mixture into the $C_7$ olefin stream and the recycle stream. Such techniques can include, but are not limited to, extraction, filtration, evaporation, or distillation, as well as combinations of two or more of these techniques. In particular aspects of this invention, step (b) utilizes distillation at any suitable distillation conditions (and one or more than one distillation column can be used).

The reaction mixture is separated in step (b) into a desirable $C_7$ olefin stream and a recycle stream, and this recycle stream can comprise a $C_6-$ recycle stream and a $C_8+$ recycle stream. The $C_6-$ recycle stream comprises (or consists essentially of, or consists of) olefins/hydrocarbons having six or fewer carbon atoms, while the $C_8+$ recycle stream comprises (or consists essentially of, or consists of) olefins/hydrocarbons have eight or more carbon atoms.

A benefit of the disclosed process/system to produce n-heptane is a minimal amount of waste that leaves the process/system. The aforementioned recycle stream, in a particular aspect of this invention, is added into the feed mixture prior to isomerization-metathesis. Hence, the feed mixture contains 1-hexene, 1-octene, and the recycle stream in this particular aspect.

With on-going recycle, it is not uncommon for impurities in the main feedstocks (1-hexene and 1-octene) to build-up over time. To remedy this, the disclosed process can comprise a purging step in which non-olefins (e.g., alkanes) are purged from the recycle stream (e.g., from the $C_6-$ recycle stream and the $C_8+$ recycle stream) prior to adding the recycle stream into the feed mixture for isomerization-metathesis.

Referring now to step (c), the separated $C_7$ olefin stream is hydrogenated to form a product stream containing n-heptane. Typically, step (c) is performed by contacting the $C_7$ olefin stream with a suitable hydrogenation catalyst in the presence of hydrogen to form the product stream comprising n-heptane. The hydrogenation catalyst used in step (c) of the process to produce n-heptane is not particularly limited, so long as such catalyst is able to efficiently convert $C_7$ olefins to n-heptane, as described herein. In one aspect, the hydrogenation catalyst can contain platinum, rhenium, palladium, nickel, or copper, and the like, as well as any combination thereof. In another aspect, the hydrogenation catalyst contains platinum; alternatively, rhenium; alternatively, palladium; alternatively, nickel; or alternatively, copper. Illustrative hydrogenation catalyst systems and reaction conditions are described, for instance, in Chetty et al., American Chemical Society Omega 2018, 3, 7911-7924; and U.S. Pat. No. 5,093,535.

While not being limited thereto, the hydrogenation in step (c) can utilize a copper-based catalyst system. One such copper-based catalyst system can comprise Cu/alumina with any suitable amount of copper, such as from 1 to 35 wt. % copper based on the weight of the supported catalyst. In some aspects, the amount of copper in the Cu/alumina catalyst falls within a range from 2 to 30 wt. %, or from 5 to 25 wt. %, and the like. Likewise, the hydrogenation in step (c) can utilize a supported nickel catalyst system, with any suitable support (e.g., solid oxide support) and any suitable loading of nickel.

The temperature and pressure conditions used for the hydrogenation step are not particularly limited. Generally, however, the hydrogenation temperature can be in a range from 80 to 200° C.; alternatively, from 90 to 190° C.; or alternatively, from 100 to 180° C. The hydrogenation pressure can be in a range from 10 to 70 bar; alternatively, from 20 to 50 bar; or alternatively, from 25 to 45 bar. These temperature and pressure ranges also are meant to encompass circumstances where step (c) is conducted at a series of different temperatures and pressures instead of at a single fixed temperature and a single fixed pressure, wherein at least one temperature and pressure fall within the respective ranges.

In one aspect, the molar ratio of hydrogen ($H_2$) to the $C_7$ olefin stream in step (c) can fall within a range from 0.5:1 to 5:1, while in another aspect, the molar ratio of hydrogen to the $C_7$ olefin stream can range from 0.75:1 to 3:1, and in yet another aspect, the molar ratio of hydrogen to the $C_7$ olefin stream can range from 1:1 to 2:1. As those skilled in the art would readily recognize, the molar ratio of hydrogen ($H_2$) to $C_7$ olefins can change as the hydrogenation reaction proceeds. Accordingly, these ranges of molar ratios are meant to encompass the initial ratio as well as any molar ratio of hydrogen to $C_7$ olefins encountered as the hydrogenation reaction proceeds.

After separating step (b) and hydrogenating step (c), the n-heptane can have a purity of at least 90 wt. %, at least 95 wt. %, at least 98 wt. %, at least 99 wt. %, at least 99.5 wt. %, or at least 99.9 wt. %, in the product stream. The purity is based on the weight of the n-heptane in the product stream to the total weight of the product stream.

Optionally, the process to produce n-heptane can further comprise a step of determining an average molecular weight of the feed mixture, and adjusting a feed ratio of 1-hexene:1-octene based on the average molecular weight. Hence, the feed ratio of 1-hexene:1-octene subjected to isomerization-metathesis can be adjusted, manually and/or automatically, based on the determined average molecular weight of the feed mixture, including the recycle stream—which can comprise a $C_6-$ recycle stream and a $C_8+$ recycle stream. As an example, if the target weight ratio of 1-hexene:1-octene is 42:58 (molar ratio of 1-hexene:1-octene of approximately 1:1.04 and an average molecular weight of 98.4 g/mol total olefin), for instance, and if there is a higher amount of $C_6-$ than $C_8+$ in the overall recycle stream such that the average molecular weight of the overall feed mixture is less than that for a weight ratio of 1-hexene:1-octene equal to 42:58 (i.e., 98.4 g/mol total olefin), then the amount of 1-octene in the feed mixture can be increased to bring the average molecular weight up to the target value of 98.4 g/mol total olefin. This invention is not limited by the technique or methodology used to determine the average molecular weight.

Consistent with aspects of this invention, a single pass yield to n-heptane (in the product stream) in the disclosed process to produce n-heptane can range from 4 to 20 wt. %, such as from 5 to 15 wt. %, or from 7 to 12 wt. %. This yield is based on the total weight of the feed mixture. Additionally or alternatively, a single pass yield to $C_7$ olefins (in the reaction mixture) in the disclosed process to produce n-heptane can range from 4 to 20 wt. %, such as from 5 to 15 wt. %, or from 7 to 12 wt. %. This yield also is based on the total weight of the feed mixture.

Manufacturing Systems

A n-heptane manufacturing system consistent with aspects of the present invention can comprise (or consist essentially of, or consist of) (i) a reactor configured to produce a reaction mixture containing $C_7$ olefins from a reactor feed stream comprising 1-hexene, 1-octene, and a recycle stream, (ii) a separations system configured to fractionate the reaction mixture into a $C_7$ olefin stream and the recycle stream, and (iii) a hydrogenation unit configured to produce a product stream containing n-heptane from the $C_7$ olefin stream and hydrogen. Generally, the features of this system for manufacturing n-heptane (e.g., the reactor, the reactor feed stream, the conditions under which the reaction mixture is formed, the separations system and its components, the hydrogenation unit and the conditions under which the product stream is performed, among others) are independently described herein and these features can be combined in any combination to further describe the disclosed system for manufacturing n-heptane. Moreover, additional components or devices can be present in this system, and can be utilized without limitation and in any combination to further describe the system for manufacturing n-heptane, unless stated otherwise.

The (i) reactor in the n-heptane manufacturing system can be any reactor that is suitable for and capable of producing a reaction mixture containing $C_7$ olefins from a reactor feed stream comprising 1-hexene, 1-octene, and a recycle stream. In one aspect, the reactor can be configured to contact the reactor feed stream with a catalyst to form the reaction mixture, while in another aspect, the reactor can be a fixed bed reactor configured to contact the reactor feed stream with a catalyst to form the reaction mixture.

As disclosed hereinabove, the catalyst can be an isomerization-metathesis catalyst, inclusive of a suitable transition metal supported on a suitable support, such as a solid oxide, examples of which can include, but are not limited to, silica, alumina, silica-alumina, aluminum phosphate, zinc aluminate, zirconia, thoria, and the like, or combinations thereof. For instance, the isomerization-metathesis catalyst can contain tungsten, molybdenum, rhenium, or ruthenium, and the like, as well as any combination thereof; alternatively, tungsten; alternatively, molybdenum; alternatively, rhenium; or alternatively, ruthenium. A particularly suitable isomerization-metathesis catalyst for use in the reactor (e.g., fixed bed reactor) in the n-heptane manufacturing system is a tungsten/silica catalyst.

The reactor is generally configured to operate at any of the temperature, pressure, and WHSV values disclosed hereinabove. Thus, the reactor can be configured to operate at a temperature in a range from 200° C. to 500° C. (e.g., from 225° C. to 475° C., from 250° C. to 400° C., or from 270° C. to 350° C.), a pressure in a range from 500 to 2000 psig (e.g., from 700 to 1800 psig, from 800 to 1600 psig, or from 1000 to 1500 psig), and a WHSV in a range from 0.01 to 5 hr$^{-1}$ (e.g., from 0.05 to 4, from 0.1 to 5, from 0.5 to 4, or from 1 to 3).

The n-heptane manufacturing system (or the reactor) is capable of producing (or configured to produce) an amount of $C_7$ olefins in a reasonable single pass yield, typically in the 4 to 20 wt. % range, based on the total weight of the reactor feed stream, although not limited thereto. Thus, the system (or reactor) can be configured to produce the reaction mixture containing $C_7$ olefins in a single pass yield of from 4 to 20 wt. %, and in some aspects, in a single pass yield ranging from 5 to 15 wt. % or from 7 to 12 wt. %. This yield is based on the weight of $C_7$ olefins produced in the reactor and present in the reaction mixture, based on the total weight of the reactor feed stream.

The (ii) separations system for fractionating the reaction mixture into a $C_7$ olefin stream and the recycle stream is not particularly limited, and can include any suitable separations apparatus either alone or in combination, such as an extraction unit, a filtration unit, an evaporator, a distillation column, and the like. For instance, the separations system of the n-heptane manufacturing system can include two distillation columns. In one aspect, the first distillation column can be configured to form a $C_7-$ overhead stream and a $C_8+$ bottoms stream from the reaction mixture, and the second distillation column can be configured to form a $C_6-$ overhead stream and the $C_7$ olefin stream from the $C_7-$ overhead stream. In another aspect, the first distillation column can be configured to form a $C_6-$ overhead stream and a $C_7+$ bottoms stream from the reaction mixture, and the second distillation column can be configured to form the $C_7$ olefin stream and a $C_8+$ bottoms stream from the $C_7+$ bottoms stream. The respective distillation columns can be configured to operate at any suitable temperature, pressure, number of stages. For example, in circumstances where the first distillation column is configured to form a $C_6-$ overhead stream and a $C_7+$ bottoms stream from the reaction mixture, at atmospheric pressure, $C_2-C_3$ olefins will flash easily, and the $C_6-$ olefins will be taken overhead at a maximum bottoms temperature of approximately 138° C. Subsequently, the second distillation column is configured to form the $C_7$ olefin stream (overhead) and a $C_8+$ bottoms stream from the $C_7+$ bottoms stream. Also at atmospheric pressure, the $C_7$ olefins will go overhead at a bottoms temperature of approximately 156° C.

Although not required, in an advantageous aspect of this invention, the n-heptane manufacturing system can further include a recycle loop, which can be configured to convey the recycle stream from the separations system and to add the recycle stream into the reactor feed stream prior to entering the reactor. The recycle stream can contain a $C_6-$ recycle stream and a $C_8+$ recycle stream (respectively, the $C_6-$ stream and the $C_8+$ stream from the distillation columns). Optionally, the n-heptane manufacturing system can further include a $C_6-$ purge line and/or a $C_8+$ purge line from the recycle stream (e.g., respectively, from the $C_6-$ recycle stream and the $C_8+$ recycle stream). The purge lines are configured to remove non-olefinic materials, such as alkanes, that may accumulate in the manufacturing system over time.

Also optionally, the n-heptane manufacturing system can further include a back-up reactor, which can be substantially the same as the (i) reactor disclosed hereinabove. The back-up reactor can be used in the manufacturing system when the (i) reactor is out of service for maintenance, for catalyst regeneration, and so forth. The back-up reactor generally is positioned in parallel with the (i) reactor, such that swapping from one to other is relatively easy.

The (iii) hydrogenation unit in the n-heptane manufacturing system generally can be configured to produce a product stream containing n-heptane from the $C_7$ olefin stream (discharged from the separations system, e.g., the distillation columns) and hydrogen. The (iii) hydrogenation unit in the n-heptane manufacturing system can be any hydrogenation unit that is suitable for and capable of producing a product stream containing n-heptane from the $C_7$ olefin stream and hydrogen. Generally, the hydrogenation unit is configured to contact the olefin stream, hydrogen, and a suitable catalyst to form the product stream containing n-heptane. As disclosed hereinabove, the hydrogenation catalyst can contain platinum, rhenium, palladium, nickel, or copper, and the like, as well as any combination thereof; alternatively, platinum; alternatively, rhenium; alternatively, palladium; alternatively, nickel; or alternatively, copper.

Beneficially, the n-heptane manufacturing system can produce n-heptane in very high purity. For instance, the n-heptane manufacturing system is capable of forming (or configured to form) the product stream at a purity of n-heptane in the product stream of at least 90 wt. %, and more often, at least 95 wt. % or at least 98 wt. %, and in some instances, at least 99 wt. %, at least 99.5 wt. %, or at least 99.9 wt. %. The purity is based on the weight of n-heptane in the product stream based on the total weight of the product stream.

Optionally, the manufacturing system can further comprise a control system, and the control system can be configured to determine an average molecular weight of the reactor feed stream, and also configured to adjust a feed ratio of 1-hexene:1-octene based on the average molecular weight. The average molecular weight can be determined using any suitable analytical technique, thus the control system can comprise any analytical instrument or device that is capable of determining the average molecular weight of the reactor feed stream (which contains 1-hexene, 1-octene, and the recycle stream).

The control system, which can comprise any suitable processing unit or computer system, can be used to analyze the data regarding the average molecular weight, and adjust the feed ratio of 1-hexene:1-octene based on the determined molecular weight. In an aspect, the control system can be programmed with an algorithm to control the feed ratio based on the average molecular weight determined by the analytical instrument or device.

The control system can be operated on an as-needed basis, at set time intervals, or continuously, depending upon the requirements of the manufacturing system. Thus, it is contemplated that the feed ratio in the reactor feed stream can be monitored and/or adjusted and/or controlled continuously. Accordingly, in particular aspects consistent with this invention, the manufacturing system and the control system can operate in real-time or near real-time, such that the average molecular weight can be determined, and that determined molecular weight can be used, instantaneously or nearly instantaneously, to adjust the feed ratio.

The control system can be implemented using a personal computer, a network computer, a server, a mainframe, or other similar microcomputer-based workstation. The control system can comprise any computer operating environment, such as hand-held devices, multiprocessor systems, microprocessor-based or programmable sender electronic devices, minicomputers, mainframe computers, and the like. The control system device also can be practiced in distributed computing environments where tasks are performed by remote processing devices. Furthermore, the control system can comprise a mobile terminal, such as a smart phone, a cellular telephone, a cellular telephone utilizing wireless application protocol (WAP), personal digital assistant (PDA), intelligent pager, portable computer, a hand held computer, a conventional telephone, a wireless fidelity (Wi-Fi) access point, or a facsimile machine. The aforementioned systems and devices are examples, and the control system can comprise any other suitable device, technology, or control scheme.

Referring now to FIG. 1, which illustrates n-heptane manufacturing system 100 consistent with an aspect of the present invention. The n-heptane manufacturing system 100 can include 1-hexene feed tank 102, 1-octene feed tank 108, reactor 120 with fixed bed of catalyst 122, first distillation column 130, second distillation column 150, hydrogenation unit 170, and controller 180. In system 100, 1-hexene feed stream 104 from the 1-hexene feed tank 102 is fed through 1-hexene pump 106, while 1-octene feed stream 110 from the 1-octene feed tank 108 is fed through 1-octene pump 112, and these are combined to form reactor feed stream 114 (also referred to as the feed mixture), which is heated to a suitable reaction temperature via reactor feed stream heater 116 and subsequently introduced into the reactor 120. Exiting the reactor 120 are light stream 124 (which can contain volatile low boiling compounds) and reaction mixture 126, which contains $C_7$ olefins.

In FIG. 1, the reaction mixture 126 exiting the reactor 120 optionally can be heated (using reactor feed stream heater 116) and is introduced into the first distillation column 130. Exiting the first distillation column 130 are $C_7-$ overhead stream 132—which passes through condenser 134 and enters the second distillation column 150—and $C_8+$ bottoms stream 136, part of which can form a heavies recycle stream 138, and after heavies heat exchanger 142, is reintroduced into the first distillation column 130. From the $C_8+$ bottoms stream 136, $C_8+$ recycle stream 144 is recycled and combined into the reactor feed stream 114 prior to the reactor 120. Heavy $C_8+$ purge line 146 can withdraw alkane and other non-olefinic materials from the $C_8+$ recycle stream 144. The $C_7-$ overhead stream 132 enters the second distillation column 150 and $C_6-$ overhead stream 152 and $C_7$ olefin (heptene) stream 160 are discharged. The $C_6-$ overhead stream 152 passes through condenser 154 to form $C_6-$ recycle stream 156 (also termed the lights recycle stream), which is recycled and combined into the reactor feed stream 114 prior to the reactor 120. Light $C_6-$ purge line 158 can withdraw alkane and other non-olefinic materials from the $C_6-$ recycle stream 156.

From the $C_7$ olefin (heptene) stream 160, part of which can form heptene recycle stream 162, and after heptene stream heat exchanger 164, is reintroduced into the second distillation column 150. The $C_7$ olefin (heptene) stream 160 enters pre-hydrogenation heater 166 and then is introduced into the hydrogenation unit 170. In the hydrogenation unit 170, heptene is combined with hydrogen feed stream 172 in the presence of a suitable catalyst to from product stream 174 containing n-heptane, which is transferred to n-heptane storage tank 176.

In FIG. 1, information or data 182 on parameters in the n-heptane manufacturing system 100, such as information or data on the average molecular weight of the reactor feed stream 114 determined by a suitable analytical device (not shown) can be provided to the controller 180, which can then control or adjust 184 any operational parameter within the n-heptane manufacturing system 100, such as adjusting 184 a feed ratio of 1-hexene:1-octene in the reactor feed stream 114 based on (or according to) the average molecular weight determined by the analytical device. For example, if the target weight ratio of 1-hexene:1-octene is 42:58 (molar ratio of 1-hexene:1-octene of approximately 1:1.04 and an average molecular weight of 98.4 g/mol total olefin), and if there is a higher amount of $C_6-$ than $C_8+$ in the recycle stream such that the average molecular weight of the overall feed mixture is less than that for a weight ratio of 1-hexene:1-octene equal to 42:58 (i.e., 98.4 g/mol total olefin), then the controller 180 can adjust 184 (increase) the amount of 1-octene in the reactor feed stream 114, such that the average molecular weight is increased up to the target value. The system 100 and controller 180 can employ any suitable technique or methodology to determine the average molecular weight.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

For the n-heptane manufacturing system 100 of FIG. 1, a computer simulation was performed. The catalyst utilized is an isomerization-metathesis catalyst available under the grade designation of Lynx® X-053, a tungsten/silica catalyst from BASF (tungsten oxide on silica granules, 88-94 wt. % silica, 6-12 wt. % tungsten oxide).

The feed stream contains 1-hexene and 1-octene mixed in a weight ratio of 42:58 (not 50:50), and is preheated to 285-290° C. and fed across a fixed catalyst bed of X-053 catalyst, which is capable of inducing metathesis of the olefins and isomerizing the olefins as well. For the simulation, a WHSV of 2 hr$^{-1}$ in the reactor is used, and a final n-heptane purity in the product stream of 99 wt. %. The system operates in a steady-state equilibrium in which a portion of the production yields $C_7$ olefins (internal and terminal olefins, including n-heptene). The reactor effluent is fed into a series of distillation columns. The first distillation column separates $C_7$ and lighter fractions from heavy materials, and the second distillation column separates n-heptene from the lights. The bottoms from the second column is hydrogenated to the desired n-heptane product. The remaining material from both distillation columns (e.g., higher and lower carbon number olefins) is then recycled back to the front of the reactor and combined with fresh hexene/octene feed.

Initially, the amount of $C_7$ in the reaction effluent is ~14.5 wt. %, but as heptene is removed from the system (and hydrogenated to form n-heptane), the amount of $C_7$ that is removed is replaced with an equivalent weight of the mixture of hexene/octene. Based on the computer simulation and after reaching a steady-state equilibrium over time, approximately 8-9 wt. % of the reactor effluent discharged from the reactor is heptene (a single pass yield). After each pass, $C_7$'s are removed and hydrogenated, and the recycle stream is mixed again with a fresh mixture of hexene/octene after each pass, resulting in the steady-state distribution of the reactor effluent shown in Table I.

TABLE I

| Carbon Number | wt. % |
|---|---|
| 2 | <0.1 |
| 3 | 0.7 |
| 4 | 8.8 |
| 5 | 12.8 |
| 6 | 14.8 |
| 7 | 8.8 |
| 8 | 13.9 |
| 9 | 10.7 |
| 10 | 7.9 |
| 11 | 6.1 |
| 12 | 4.6 |
| 13 | 3.2 |
| 14 | 2.6 |
| 15 | 1.4 |
| 16 | 1.0 |
| 17 | 0.9 |
| 18 | 0.7 |
| 19 | 0.4 |
| 20 | 0.2 |
| 21 | 0.1 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process comprising:
(a) subjecting a feed mixture comprising 1-hexene and 1-octene to isomerization-metathesis to form a reaction mixture containing $C_7$ olefins;
(b) separating the reaction mixture into a $C_7$ olefin stream and a recycle stream; and
(c) hydrogenating the $C_7$ olefin stream to form a product stream containing n-heptane.

Aspect 2. The process defined in aspect 1, wherein step (a) is conducted at any suitable temperature, e.g., from 200° C. to 500° C., from 250° C. to 400° C., or from 270° C. to 350° C.

Aspect 3. The process defined in aspect 1 or 2, wherein step (a) is conducted at any suitable pressure, e.g., from 500 to 2000 psig, from 700 to 1800 psig, or from 900 to 1500 psig.

Aspect 4. The process defined in any one of the preceding aspects, wherein step (a) comprising contacting the feed mixture with an isomerization-metathesis catalyst to form the reaction mixture.

Aspect 5. The process defined in any one of the preceding aspects, wherein step (a) comprising contacting the feed mixture with a fixed bed of an isomerization-metathesis catalyst to form the reaction mixture.

Aspect 6. The process defined in aspect 5, wherein the feed mixture and the catalyst are contacted at any suitable WHSV, e.g., from 0.1 to 5 $hr^{-1}$, from 0.5 to 4 $hr^{-1}$, or from 1 to 3 $hr^{-1}$.

Aspect 7. The process defined in any one of aspects 4-6, wherein the isomerization-metathesis catalyst comprises any suitable supported catalyst, e.g., containing tungsten, molybdenum, rhenium, or ruthenium, or a combination thereof, supported on a suitable support, such as a tungsten/silica catalyst.

Aspect 8. The process defined in any one of the preceding aspects, wherein a weight ratio of 1-hexene:1-octene in the feed mixture is in any suitable range, e.g., from 30:70 to 70:30, from 35:65 to 65:35, from 35:65 to 50:50, from 40:60 to 60:40, or from 40:60 to 45:55.

Aspect 9. The process defined in any one of the preceding aspects, wherein a single pass yield to n-heptane is any suitable single pass yield, e.g., from 4 to 20 wt. %, from 5 to 15 wt. %, or from 7 to 12 wt. %, based on the total weight of the feed mixture.

Aspect 10. The process defined in any one of the preceding aspects, wherein separating in step (b) comprises any suitable technique, e.g., extraction, filtration, evaporation, or distillation, or any combination thereof, to form the $C_7$ olefin stream and the recycle stream.

Aspect 11. The process defined in any one of the preceding aspects, wherein separating in step (b) comprises distillation.

Aspect 12. The process defined in any one of the preceding aspects, wherein the recycle stream comprises a $C_6$– recycle stream and a $C_8$+ recycle stream.

Aspect 13. The process defined in any one of the preceding aspects, wherein the recycle stream is added into the feed mixture, e.g., the feed mixture contains 1-hexene, 1-octene, and the recycle stream.

Aspect 14. The process defined in any one of the preceding aspects, further comprising a step of purging non-olefins (e.g., alkanes) from the recycle stream ($C_6$– recycle stream and $C_8$+ recycle stream) prior to adding into the feed mixture.

Aspect 15. The process defined in any one of the preceding aspects, wherein step (c) comprising contacting the $C_7$ olefin stream with a suitable hydrogenation catalyst in the presence of hydrogen to form the product stream comprising n-heptane.

Aspect 16. The process defined in aspect 15, wherein the hydrogenation catalyst comprises platinum, rhenium, palladium, nickel, or copper, or any combination thereof.

Aspect 17. The process defined in any one of the preceding aspects, wherein a purity of the n-heptane in the product stream is any suitable purity, e.g., at least 90 wt. %, at least 95 wt. %, at least 98 wt. %, at least 99 wt. %, at least 99.5 wt. %, or at least 99.9 wt. %, based on the total weight of the product stream.

Aspect 18. The process defined in any one of the preceding aspects, further comprising a step of determining an average molecular weight of the feed mixture, and adjusting a feed ratio of 1-hexene:1-octene based on the average molecular weight (e.g., if the average molecular weight is low, increase the relative amount of 1-octene present in the feed mixture).

Aspect 19. A n-heptane manufacturing system comprising:
(i) a reactor configured to produce a reaction mixture containing $C_7$ olefins from a reactor feed stream comprising 1-hexene, 1-octene, and a recycle stream;
(ii) a separations system configured to fractionate the reaction mixture into a $C_7$ olefin stream and the recycle stream; and
(iii) a hydrogenation unit configured to produce a product stream containing n-heptane from the $C_7$ olefin stream and hydrogen.

Aspect 20. The system defined in aspect 19, wherein the system further comprises a recycle loop configured to convey the recycle stream from the separations system and to add the recycle stream into the reactor feed stream.

Aspect 21. The system defined in aspect 19 or 20, wherein the recycle stream comprises a $C_6$– recycle stream and a $C_8$+ recycle stream.

Aspect 22. The system defined in any one of aspects 19-21, wherein the separations system comprises two distillation columns.

Aspect 23. The system defined in aspect 22, wherein a first distillation column is configured to form a $C_7-$ overhead stream and a $C_8+$ bottoms stream from the reaction mixture, and a second distillation column is configured to form a $C_6-$ overhead stream and the $C_7$ olefin stream from the $C_7-$ overhead stream.

Aspect 24. The system defined in aspect 22, wherein a first distillation column is configured to form a $C_6-$ overhead stream and a $C_7+$ bottoms stream from the reaction mixture, and a second distillation column is configured to form the $C_7$ olefin stream and a $C_8+$ bottoms stream from the $C_7+$ bottoms stream.

Aspect 25. The system defined in any one of aspects 19-24, wherein the system further comprises a control system, the control system configured to determine an average molecular weight of the reactor feed stream, and configured to adjust a feed ratio of 1-hexene:1-octene based on the average molecular weight.

Aspect 26. The system defined in any one of aspects 19-25, wherein the system further comprises a $C_6-$ purge line and/or a $C_8+$ purge line from the recycle stream for removing non-olefinic materials, e.g., alkanes.

Aspect 27. The system defined in any one of aspects 19-26, wherein the reactor is configured to contact the reactor feed stream with a catalyst to form the reaction mixture.

Aspect 28. The system defined in any one of aspects 19-27, wherein the reactor is a fixed bed reactor configured to contact the reactor feed stream with a catalyst to form the reaction mixture.

Aspect 29. The system defined in aspect 27 or 28, wherein the catalyst comprises a supported isomerization/metathesis catalyst, e.g., containing tungsten, molybdenum, rhenium, or ruthenium, or a combination thereof, such as a tungsten/silica catalyst.

Aspect 30. The system defined in any one of aspects 19-29, wherein the reactor is configured to operate at a temperature in a range from 200° C. to 500° C., a pressure in a range from 500 to 2000 psig, and a WHSV in a range from 0.1 to 5 $hr^{-1}$.

Aspect 31. The system defined in any one of aspects 19-30, wherein the system further comprises a back-up reactor, the back-up reactor positioned in parallel with the reactor.

Aspect 32. The system defined in any one of aspects 19-31, wherein the reactor (or system) is configured to produce the reaction mixture containing $C_7$ olefins in any suitable single pass yield, e.g., from 4 to 20 wt. %, from 5 to 15 wt. %, or from 7 to 12 wt. %, based on the total weight of the reactor feed stream.

Aspect 33. The system defined in any one of aspects 19-32, wherein the system is capable of forming the product stream at any suitable purity of the n-heptane in the product stream, e.g., at least 90 wt. %, at least 95 wt. %, at least 98 wt. %, at least 99 wt. %, at least 99.5 wt. %, or at least 99.9 wt. %, based on the total weight of the product stream.

We claim:

1. A n-heptane manufacturing system comprising:
   (i) a reactor configured to contact a reactor feed stream comprising 1-hexene, 1-octene, and a recycle stream with an isomerization-metathesis catalyst to form a reaction mixture containing $C_7$ olefins;
   (ii) a separations system configured to receive the reaction mixture from the reactor and to fractionate the reaction mixture into a $C_7$ olefin stream and the recycle stream, wherein the separations system comprises one or more distillation columns;
   (iii) a hydrogenation unit configured to receive the $C_7$ olefin stream from the separations system and a hydrogen stream and to contact the $C_7$ olefin stream and the hydrogen stream with a hydrogenation catalyst to produce a product stream containing n-heptane; and
   (iv) a recycle loop configured to convey the recycle stream from the separations system and to add the recycle stream into the reactor feed stream.

2. The system of claim 1, wherein the recycle stream comprises a $C_6-$ recycle stream and a $C_8+$ recycle stream.

3. The system of claim 1, wherein the separations system comprises a first distillation column configured to form a $C_7-$ overhead stream and a $C_8+$ bottoms stream from the reaction mixture, and a second distillation column configured to form a $C_6-$ overhead stream and the $C_7$ olefin stream from the $C_7-$ overhead stream.

4. The system of claim 1, wherein the separations system comprises a first distillation column configured to form a $C_6-$ overhead stream and a $C_7+$ bottoms stream from the reaction mixture, and a second distillation column configured to form the $C_7$ olefin stream and a $C_8+$ bottoms stream from the $C_7+$ bottoms stream.

5. The system of claim 1, wherein the system further comprises a control system, the control system configured to determine an average molecular weight of the reactor feed stream, and configured to adjust a feed ratio of 1-hexene:1-octene based on the average molecular weight.

6. The system of claim 1, wherein the system further comprises:
   a $C_6-$ purge line and/or a $C_8+$ purge line from the recycle stream for removing non-olefinic materials; and
   a back-up reactor, the back-up reactor positioned in parallel with the reactor.

7. The system of claim 1, wherein:
   the reactor is a fixed bed reactor configured to contact the reactor feed stream with a supported isomerization-metathesis catalyst to form the reaction mixture; and
   the reactor is configured to operate at a temperature from 200° C. to 500° C., a pressure from 500 to 2000 psig, and a WHSV from 0.1 to 5 $hr^{-1}$.

8. The system of claim 1, wherein:
   the reactor is configured to produce the reaction mixture containing $C_7$ olefins in a single pass yield from 4 to 20 wt. %, based on the total weight of the reactor feed stream; and
   the system is capable of forming the product stream at a purity of n-heptane in the product stream of at least 95 wt. %, based on the total weight of the product stream.

9. The system of claim 1, wherein:
   the reactor is configured to produce the reaction mixture containing $C_7$ olefins in a single pass yield from 7 to 12 wt. %, based on the total weight of the reactor feed stream; and
   the system is capable of forming the product stream at a purity of n-heptane in the product stream of at least 99 wt. %, based on the total weight of the product stream.

10. The system of claim 1, wherein the separations system comprises two distillation columns.

11. The system of claim 1, wherein the isomerization-metathesis catalyst comprises a supported isomerization-metathesis catalyst containing tungsten, molybdenum, rhenium, ruthenium, or a combination thereof.

12. The system of claim 1, wherein the system further comprises a back-up reactor, the back-up reactor positioned in parallel with the reactor.

13. The system of claim 1, wherein:
the system further comprises a recycle loop configured to convey the recycle stream from the separations system and to add the recycle stream into the reactor feed stream; and
the recycle stream comprises a $C_6-$ recycle stream and a $C_8+$ recycle stream.

14. The system of claim 1, wherein:
the reactor is configured to produce the reaction mixture containing $C_7$ olefins in a single pass yield from 5 to 15 wt. %, based on the total weight of the reactor feed stream; and
the system is capable of forming the product stream at a purity of n-heptane in the product stream of at least 98 wt. %, based on the total weight of the product stream.

15. The system of claim 14, wherein the separations system comprises a first distillation column configured to form a $C_7-$ overhead stream and a $C_8+$ bottoms stream from the reaction mixture, and a second distillation column configured to form a $C_6-$ overhead stream and the $C_7$ olefin stream from the $C_7-$ overhead stream.

16. The system of claim 14, wherein the separations system comprises a first distillation column configured to form a $C_6-$ overhead stream and a $C_7+$ bottoms stream from the reaction mixture, and a second distillation column configured to form the $C_7$ olefin stream and a $C_8+$ bottoms stream from the $C_7+$ bottoms stream.

17. The system of claim 14, wherein the system further comprises a control system, the control system configured to determine an average molecular weight of the reactor feed stream, and configured to adjust a feed ratio of 1-hexene:1-octene based on the average molecular weight.

18. The system of claim 1, wherein the reactor is a fixed bed reactor configured to contact the reactor feed stream with a supported isomerization-metathesis catalyst to form the reaction mixture.

* * * * *